(12) United States Patent
Yoshiyuki

(10) Patent No.: US 9,448,149 B2
(45) Date of Patent: Sep. 20, 2016

(54) METHOD FOR ULTRASONIC FATIGUE TESTING AT HIGH TEMPERATURE, AND TESTING DEVICE

(75) Inventor: Furuya Yoshiyuki, Tsukuba (JP)

(73) Assignee: National Institute For Materials Science, Ibaraki (JP)

(*) Notice: Subject to any disclaimer, the term of this patent is extended or adjusted under 35 U.S.C. 154(b) by 435 days.

(21) Appl. No.: 13/985,124

(22) PCT Filed: Feb. 8, 2012

(86) PCT No.: PCT/JP2012/052881
§ 371 (c)(1),
(2), (4) Date: Oct. 25, 2013

(87) PCT Pub. No.: WO2012/111509
PCT Pub. Date: Aug. 23, 2012

(65) Prior Publication Data
US 2014/0174184 A1    Jun. 26, 2014

(30) Foreign Application Priority Data
Feb. 15, 2011   (JP) .............................. 2011-029557

(51) Int. Cl.
*G01N 3/32* (2006.01)
*G01N 29/22* (2006.01)
(Continued)

(52) U.S. Cl.
CPC ............... *G01N 3/32* (2013.01); *G01N 29/12* (2013.01); *G01N 29/228* (2013.01);
(Continued)

(58) Field of Classification Search
CPC ...... G01N 3/32; G01N 29/12; G01N 29/228; G01N 29/2418; G01N 2203/0005; G01N 2203/0008; G01N 2203/0226; G01N 2291/02827; G01N 2291/0258; G01N 2203/0658

USPC .......................................................... 73/577
See application file for complete search history.

(56) References Cited

U.S. PATENT DOCUMENTS 3,973,122 A * 8/1976 Goldberg ........... G01B 11/0625
250/338.1
5,112,137 A * 5/1992 Wickersheim ............ G01J 1/58
374/131
(Continued)

FOREIGN PATENT DOCUMENTS

SU              1059504       * 12/1983

OTHER PUBLICATIONS

Bathias et al., "Gigacycle Fatigue in Mechanical Practice", New York, Marcel Dekker, 2004, pp. 9-21.
(Continued)

*Primary Examiner* — J M Saint Surin
(74) *Attorney, Agent, or Firm* — Wenderoth, Lind & Ponack, L.L.P.

(57) ABSTRACT

Disclosed are a method for ultrasonic fatigue testing at high temperature and a testing device without needing preliminary Young's modulus measurement, and a method for ultrasonic fatigue testing at high temperature and a testing device capable of securing heat insulation for protecting a vibrator without water cooling of a horn, measuring end surface displacement of a test specimen in a noncontact manner, and solving problems of a noncontact temperature measurement of a test specimen and temperature control. Young's modulus is calculated by inverse calculation, a rod and a horn having heat resistance, heat insulation, and temperature symmetry of a test specimen are used, laser light is irradiated and received from an oblique direction to measure end surface displacement, and a noncontact temperature measurement of a test specimen by a black-body coating and a two-color radiation thermometer and temperature control by a high-frequency coil having a special shape are performed.

20 Claims, 14 Drawing Sheets

(51) Int. Cl.
*G01N 29/12* (2006.01)
*G01N 29/24* (2006.01)

(52) U.S. Cl.
CPC . *G01N 29/2418* (2013.01); *G01N 2203/0005* (2013.01); *G01N 2203/0008* (2013.01); *G01N 2203/0226* (2013.01); *G01N 2203/0658* (2013.01); *G01N 2291/0258* (2013.01); *G01N 2291/02827* (2013.01)

(56) References Cited

U.S. PATENT DOCUMENTS

| | | | | |
|---|---|---|---|---|
| 5,183,338 | A * | 2/1993 | Wickersheim | G01J 1/58 374/131 |
| 5,255,980 | A * | 10/1993 | Thomas | G01K 11/20 250/227.14 |
| 6,575,035 | B2 * | 6/2003 | Suzuki | G01L 5/0047 73/579 |
| 7,114,846 | B2 * | 10/2006 | Tominaga | G01J 5/602 250/330 |
| 7,279,218 | B2 * | 10/2007 | Watase | C09D 5/24 219/200 |
| 7,801,478 | B2 * | 9/2010 | Evans | H04N 7/163 370/278 |
| 8,063,372 | B2 * | 11/2011 | Lemieux | G01D 18/008 250/339.03 |
| 8,396,676 | B2 * | 3/2013 | Zozulya | G01N 11/16 702/50 |
| 2004/0065152 | A1 * | 4/2004 | Hull | G01N 3/32 73/579 |
| 2007/0126314 | A1 * | 6/2007 | Ohmori | G01B 3/008 310/316.01 |
| 2009/0007671 | A1 * | 1/2009 | Hull | G01M 7/025 73/579 |

OTHER PUBLICATIONS

Yi et al., "Ultrasonic fatigue of a single crystal Ni-base superalloy at 1000° C.", Materials Science and Engineering A, vol. 443, 2007, pp. 142-149.

Sawada et al., "Effect of microstructure on elastic property at high temperatures in ferritic heat resistant steels", Materials Science and Engineering A, vol. 394, 2005, pp. 36-42.

Kobayashi et al., "Low and high-cycle fatigue properties of 12Cr-2W ferritic steel at high temperature", Journal of Materials Science, vol. 39, 2004, pp. 6253-6256.

Muto et al., "High Temperature Fatigue Property and Fracture Surface Morphologies of Single Crystal Ni-Base Superalloy", 2004, pp. 185-188, with English abstract.

* cited by examiner

REFLECTION OF LASER LIGHT

REFLECTION OF LASER LIGHT

REFLECTION OF LASER LIGHT

REFLECTION OF LASER LIGHT

FIG. 5A DOUBLE-WOUND COIL WITH LARGE WIDTH

FIG. 5B DOUBLE-WOUND COIL WITH SMALL WIDTH

12Cr-2W

TMS138A

IN CASE OF SINGLE-COLOR TYPE

IN CASE OF TWO-COLOR TYPE

IN CASE OF USING BLACK-BODY COATING IN TWO-COLOR TYPE

RESULT FOR 12Cr-2W STEEL

RESULT FOR Ni-BASE SINGLE CRYSTAL ALLOY

WHEN THERE IS FREE END

WHEN THERE IS NO FREE END

METHOD FOR ULTRASONIC FATIGUE TESTING AT HIGH TEMPERATURE, AND TESTING DEVICE

TECHNICAL FIELD

The present invention relates to a method for ultrasonic fatigue testing at high temperature, and a testing device. In particular, the present invention relates to a method and device for carrying out an ultrasonic fatigue test with high precision by a new advanced technology of control of stress amplitude to be applied to a test specimen and temperature control of the test specimen at high temperature.

BACKGROUND ART

An ultrasonic fatigue test is a fatigue testing method which uses resonance with free vibration of a test specimen (NPL 1).

The ultrasonic fatigue test is a powerful tool which can realize an ultrafast fatigue test at 20 kHz 200 cycles higher than the normal, and performs a gigacycle fatigue test $10^9$ cycles or more.

In a turbine blade, such as a gas turbine, it is known that kHz order vibration occurs during operation. In simulating fatigue due to fast vibration, it can be said that the ultrasonic fatigue test is an optimum testing method.

From this point, it is desirable to develop an ultrasonic fatigue testing device which can perform a test at high temperature. However, since this method is special, in realizing a test at high temperature, there are many problems to be solved.

The ultrasonic fatigue test is a testing method in which the entire system having a vibrator, a horn configured to expand amplitude, and a test specimen is in a resonance state to cause stress amplitude in the test specimen. FIG. 12 is a schematic view of the basic configuration of a high-temperature ultrasonic fatigue testing device. An ultrasonic fatigue testing device 100 includes horns 103 which are attached to both ends of a test specimen 106, an ultrasonic oscillation device 102 which is arranged in one horn 103, a load frame 128 which applies an average load, and a high frequency heating coil 127 which heats the test specimen 106.

In this case, the output of the ultrasonic oscillator is adjusted, and displacement amplitude (end surface displacement) of the end surface of the test specimen is controlled, thereby adjusting stress amplitude to be applied to the test specimen.

The relationship between end surface displacement and stress amplitude can be obtained by solving Expression (1) (NPL 1).

[Math. 1]

$$U''(x) + P(x)U'(x) + k^2 U(x) = 0 \quad (1)$$

[Math. 2]

$$P(x) = \frac{S'(x)}{S(x)} \quad (2)$$

[Math. 3]

$$k = 2\pi f \sqrt{\frac{\rho}{E}} \quad (3)$$

Here, U(x) denotes displacement amplitude, S(x) denotes a cross-sectional area, f denotes a resonance frequency, E denotes Young's modulus, and ρ denotes density.

When an hourglass test specimen shown in FIG. 13 is used, the cross-sectional area S(x) is expressed by Expressions (4) and (5).

[Math. 4]

$$S(x) = \frac{\pi}{4} d1^2 \cosh^2(\alpha x) \alpha = \frac{1}{L1} \cosh^{-1}\left(\frac{d2}{d1}\right), \quad (4)$$

$$0 \le x \le L1$$

[Math. 5]

$$S(x) = \frac{\pi}{4} d2^2 L1 \le x \le L1 + L2 \quad (5)$$

Here, d1 denotes a minimum part diameter, d3 denotes a shoulder part diameter, L1 denotes an R part half-length, and L2 denotes a shoulder part length.

When Expressions (1) to (5) are solved, the number of undetermined coefficients becomes four. Meanwhile, there are five environmental conditions to be satisfied including 1) displacement amplitude at the center of the test specimen is zero, 2) strain amplitude in the end surface of the test specimen is zero, 3) end surface displacement to which displacement amplitude is input at the same position, and continuity of 4) strain amplitude and 5) displacement amplitude in the boundary of an R part and a shoulder part.

That is, since the number of environmental conditions is greater than the number of undetermined coefficients by one, one of the dimensional parameters of the test specimen is restricted. This becomes a resonance condition in designing the test specimen, and the shoulder part length L2 which is most readily adjusted usually conforms to the resonance condition.

CITATION LIST

Non Patent Literature

[NPL 1] C. Bathias and P. C. Paris: Gigacycle fatigue in mechanical practice, Marcel Decker, New York, 2004.
[NPL 2] J. Z. Yi, C. J. Torbet, Q. Feng, T. M. Pollock and J. W. Jones: Ultrasonic fatigue of a single crystal Ni-base superalloy at 1000° C., Materials Science & Engineering A, 443(2007), 142-149.
[NPL 3] K. Sawada, T. Ohba, H. Kushima, and K. Kimura: Effect of microstructure on elastic property at high temperatures in ferritic heat resistant steels, Materials Science & Engineering A, 394(2005), 36-42.
[NPL 4] K. Kobayashi, K. Yamaguchi, M. Kimura and M. Hayakawa: Low and high-cycle fatigue properties of 12Cr-2W ferritic steel at high temperature, Journal of Materials Science, 39(2004), 6253-6256.
[NPL 5] Muto Shinji, Mikiya Arai, Koichi Murakami: Fracture surface morphology and high-temperature fatigue properties of Ni-base single crystal alloy, Proceedings of the 27th Symposium on Fatigue, 27(2004), 185-188.

Technical Problem

Although Expressions (1) to (5) can be analytically solved at normal room temperature, since Young's modulus depends on temperature, Young's modulus becomes a variable E(x) associated with the temperature distribution of the test specimen at high temperature.

In this case, although Expressions (1) to (5) are numerically solved, at this time, it is necessary that the correlation between temperature and Young's modulus is known. For this reason, according to the method of the related art, it is necessary to experimentally obtain Young's modulus at high temperature in advance.

When a test at high temperature exceeding 1000° C. is needed for a material, such as a turbine blade material, since the temperature of the end portion of the test specimen becomes about 600 to 700° C., heat resistance up to such temperature is needed for the horn which comes into direct contact with the test specimen (NPL 2).

Since the vibrator which is attached to the other end surface of the horn is susceptible to heat, heat insulation performance is also needed for the horn. For heat insulation, although a method in which a hole is provided in a jig to transmit cooling water therethrough for water cooling is used, in the case of the horn, since fast vibration occurs, a connection portion of a cooling water pipe may be damaged. That is, in the case of the ultrasonic fatigue test, water cooling of the horn is a risky alternative which may cause leakage of water.

Since the ultrasonic fatigue test is a testing method which controls end surface displacement to cause arbitrary stress amplitude in the test specimen, it is indispensable to measure end surface displacement after the device is calibrated. The surface displacement is usually measured using a capacitance sensor 129 shown in FIG. 14(*a*). Here, reference numeral 100 represents an ultrasonic fatigue testing device, reference numeral 102 represents an ultrasonic oscillation device, reference numeral 103 represents a horn, reference numeral 106 represents a test specimen, and reference numeral 129 represents a displacement sensor (capacitance sensor).

When there is no free end, a ring-shaped capacitance sensor 130 shown in FIG. 14(*b*) is used, thereby measuring the end surface displacement.

However, since the capacitance sensor has a small working distance (the distance to a measurement surface), it is not possible to use the capacitance sensor when a measurement target is at high temperature.

In the case of a laser displacement meter, since a working distance is large, even if a measurement target is at high temperature, a measurement is possible. However, in the case of the laser displacement meter, usually, since a measurement is made using a free end in an image shown in FIG. 14(*a*), when there is no free end, it is not possible to measure displacement.

When performing a test at high temperature, it is necessary to measure the temperature at the center of the test specimen and to control the temperature to a predetermined temperature. Although the most reliable temperature measurement method is a method which uses a thermocouple, in the case of the ultrasonic fatigue test, since disconnection due to vibration occurs, a temperature measurement using a thermocouple is not suitable.

Accordingly, as alternative means, a method which uses a radiation thermometer capable of performing a temperature measurement in a noncontact manner is considered. However, in the temperature measurement using the radiation thermometer, measurement errors associated with visual field defect and emissivity change cause a problem.

Although the radiation thermometer is a thermometer which measures temperature from the amount of infrared rays emitted from the measurement surface, since a test specimen which is normally used in an ultrasonic fatigue test has a round rod shape and the measurement surface thereof is curved, the diameter of a central part (minimum cross-sectional area part) subjected to a temperature measurement is very small, about 3 mm. For this reason, even if the visual field (measurement range) is narrowed to about 1 mm using a high-precision radiation thermometer, it is not possible to receive all infrared rays to be irradiated, and an error occurs in the measured temperature. This is a problem of visual field defect.

It is necessary to set emissivity so as to convert the amount of infrared rays to temperature. Since emissivity is significantly affected by the material or state of the measurement surface, when the test specimen is heated, emissivity changes over time due to surface oxidization. An error which occurs due to emissivity change causes a significant problem.

SUMMARY OF INVENTION

The invention has been accomplished in consideration of the above-described situation, and an object of the invention is to provide a method for ultrasonic fatigue testing at high temperature and a testing device without needing preliminary Young's modulus measurement.

Another object of the invention is to provide a method for ultrasonic fatigue testing at high temperature and a testing device capable of securing heat insulation for protecting a vibrator without needing water cooling of a horn.

Still another object of the invention is to provide a method for ultrasonic fatigue testing at high temperature and a testing device capable of measuring end surface displacement of a test specimen in a noncontact manner.

Yet another object of the invention is to provide a method for ultrasonic fatigue testing at high temperature and a testing device capable of solving problems regarding a noncontact temperature measurement of a test specimen and temperature control.

Solution to Problem

The inventors have conducted intense analyses so as to solve the above-described problems. As a result, a substantiative experiment has been made with a plurality of materials and conditions in the following configuration, and a result well-matched with the fatigue test result in the method of the related art has been obtained. That is, it has been successfully verified that a correct fatigue test result has been obtained by the testing method and device of the invention, and the invention has been completed.

In order to solve the above-described problem, there is provided a method for ultrasonic fatigue testing at high temperature, in which Young's modulus corresponding to temperature is calculated from a measurement result of a resonance frequency by inverse calculation, and a fatigue load condition is controlled.

In the method for ultrasonic fatigue testing at high temperature, it is preferable that rods and horns are attached to both ends of a test specimen to secure temperature symmetry of the test specimen.

In the method for ultrasonic fatigue testing at high temperature, it is preferable that laser light is irradiated from an oblique direction using a laser displacement meter, and laser light reflected in the same direction is received to measure end surface displacement of the test specimen.

In the method for ultrasonic fatigue testing at high temperature, it is preferable that a black-body coating is coated on the test specimen using a two-color radiation thermometer to measure and control the temperature at the center of the test specimen.

In the method for ultrasonic fatigue testing at high temperature, it is preferable that high-frequency heating is performed using a double-wound coil with a coil interval equal to or smaller than 20 mm.

There is provided an ultrasonic fatigue testing device which performs the method for ultrasonic fatigue testing at high temperature. The ultrasonic fatigue testing device includes rods which are attached to both ends of a test specimen, and horns which are provided at ends of the rods opposite to the test specimen.

Advantageous Effects of Invention

According to the invention, fatigue properties at high temperature which could be evaluated only about $10^7$ cycles in the related art can be evaluated up to a gigacycle region beyond $10^9$ cycles.

In the related art, since a fatigue test could be performed only at low speed of about 10 to 100 Hz, when evaluating fatigue due to fast vibration in a turbine blade or the like, it was necessary to neglect the effect of a frequency. In contrast, according to the invention, since a fatigue test can be performed at high speed close to actual equipment, the effect of the frequency can also be appropriately evaluated.

DESCRIPTION OF EMBODIMENTS

Hereinafter, the invention will be described in detail.

In a method for ultrasonic fatigue testing at high temperature of the invention, Young's modulus corresponding to temperature is calculated from a measurement result of a resonance frequency by inverse calculation, and a fatigue load condition is controlled.

In a high-temperature ultrasonic fatigue testing device of the related art, as will be apparent from Expression (1), Young's modulus is required to calculate stress amplitude. Meanwhile, Young's modulus is not easily measured, and in particular, a Young's modulus measurement at high temperature requires sophisticated technology.

In the ultrasonic fatigue testing device, since it is possible to measure the resonance frequency of the entire system, it is possible to obtain Young's modulus by inverse calculation. In the invention, a function of inversely calculating Young's modulus is provided, and thus a preliminary Young's modulus measurement is not required.

That is, although the shoulder part length L2 can be obtained by Expressions (1) to (5), L2 may also be obtained by a measurement using the ultrasonic fatigue testing device. The L2 values obtained by calculation and actual measurement are compared, and if Young's modulus is searched when both are identical, Young's modulus is obtained. This is the basic idea of the invention.

Density ρ which is one material constant necessary for calculation can be easily measured, and the effect of temperature is negligible. Accordingly, if Young's modulus is obtained by the method of the invention, each material constant necessary for calculation can be arranged on its own account.

Figure 1:
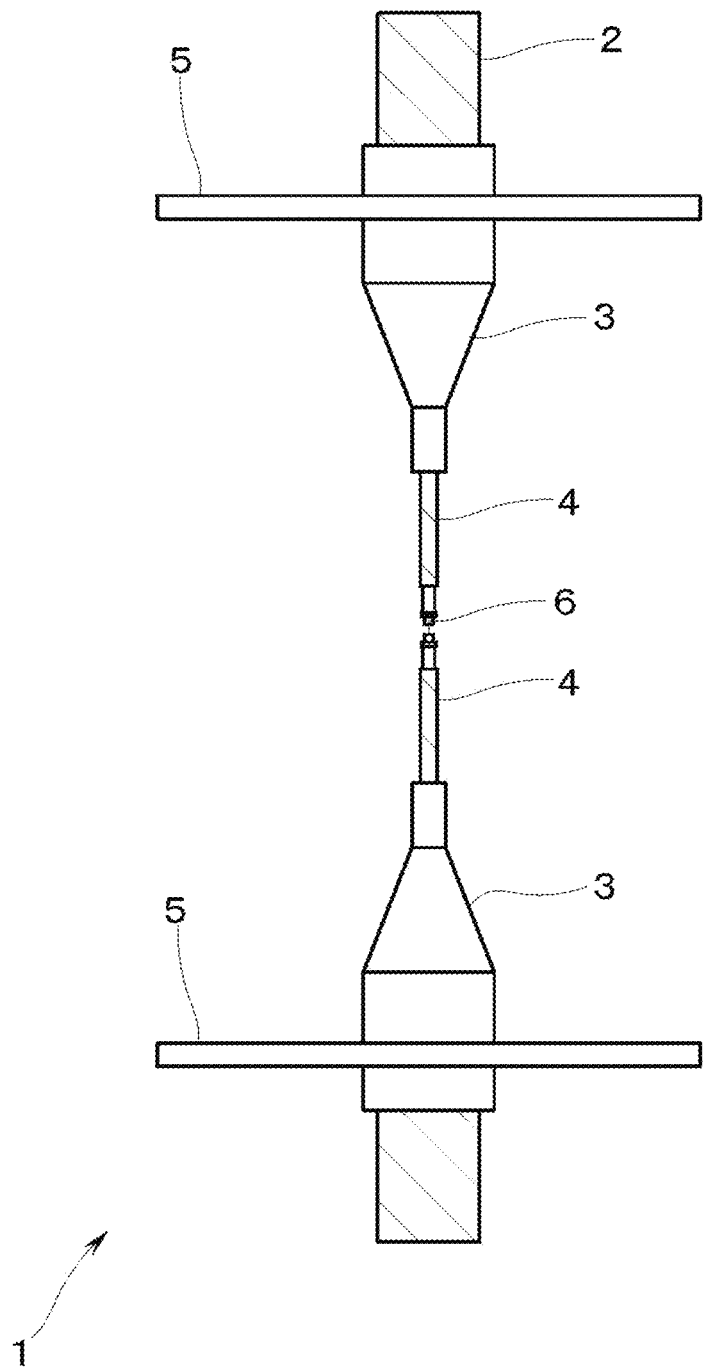
FIG. 1 is a schematic view showing an example of a testing device which is used in a method of the invention.

FIG. 1 is a schematic view showing an example of a testing device which is used in a method of the invention.

An ultrasonic fatigue testing device 1 includes ultrasonic oscillation devices 2, horns 3, rods 4, cradles 5, and a test specimen 6.

The ultrasonic oscillation device 2 includes an ultrasonic oscillator and a vibrator.

The horn 3 has the same shape as in the related art, and the rod 4 is connected to therebelow.

The cradle 5 supports the entire configuration including the ultrasonic oscillation device 2, the horn 3, the rod 4, the cradle 5, the test specimen 6, and the like.

Figure 13:
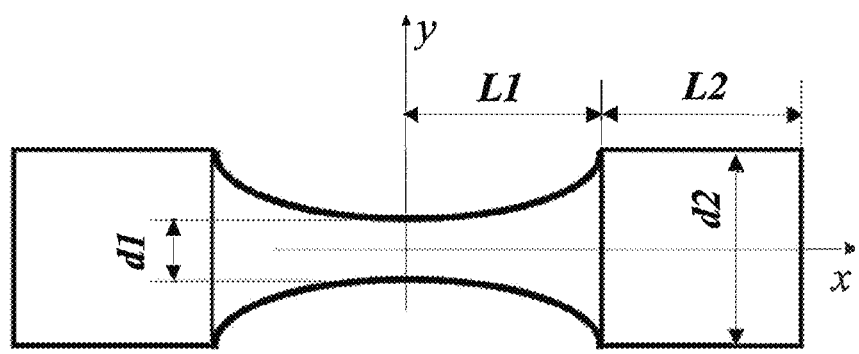
FIG. 13 shows an hourglass fatigue test specimen.
Figure 14A:
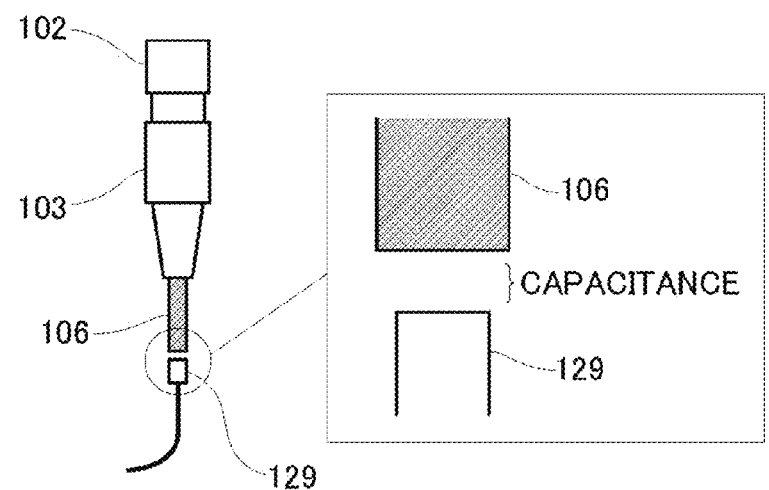
FIG. 14 is a diagram showing a mode of an end surface displacement measurement using a normal capacitance sensor.
Figure 14B:
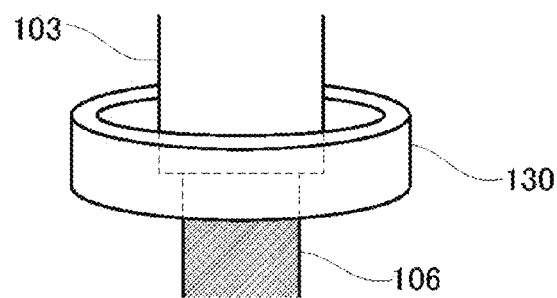

For the test specimen 6, an hourglass test specimen shown in FIG. 13 may be used.

As shown in FIG. 1, the device configuration has a feature in that the rods 4 and the horns 3 are attached to both ends of the test specimen 6, thereby securing symmetry of the temperature distribution of the test specimen.

In the device configuration disclosed in NPL 2, there is no rod 4, and one end surface of the test specimen 6 is a free end. In this case, if the center of the test specimen 6 is heated by a coil, the temperature of the end surface as the free end increases due to the difference between thermal conduction to the rod 4 and thermal conduction to the atmosphere. In this way, if the temperature distribution is asymmetrical, the distribution of Young's modulus is also asymmetrical, making it difficult to calculate stress.

In contrast, if the configuration shown in FIG. 1 is made, the temperature distribution is symmetrical in a vertical direction. Accordingly, a problem of asymmetry of the temperature distribution is resolved.

The ultrasonic fatigue testing device 1 includes the rod 4. When a test at 1000° C. is performed, the temperature at the leading end of the horn becomes 600 to 700° C. For this reason, heat resistance is needed for the horn 3, and heat insulation for protecting the vibrator of the ultrasonic oscillation device 2 is also needed. At the time of heat insulation, although water cooling of a jig is normally effective, in an ultrasonic fatigue test, the jig may be damaged due to vibration, and water cooling may result in leakage of water. Accordingly, a round bar-shaped jig (rod 4) which is formed of a heat resistant material is inserted between the test specimen 6 and the horn 3 so as to solve these problems.

When the rod 4 is designed such that the resonance frequency becomes the standard 20 kHz, the length of the rod 4 becomes about 120 mm. If the rod 4 is inserted, even when the end surface of the rod 4 in contact with the test specimen 6 becomes about 600 to 700° C., the other end surface in contact with the horn 3 becomes lower than 100° C. That is, it is possible to secure sufficient heat resistance without water cooling.

A temperature range which can be tested using the ultrasonic fatigue testing device 1 is, for example, 500 to 1500° C.

Incidentally, in the device of NPL 2, it is inferred that a position which is heated by a coil is shifted upward, thereby securing temperature symmetry. However, in this method, the distance between the center of the test specimen 6 where temperature control is performed and the heating position is extended. For this reason, it is disadvantageous in that temperature control is performed so as to follow an increase in temperature at the time of an ultrasonic test described below. From this point, the configuration of the invention in which the center of the test specimen 6 can be heated has an advantage.

Although a method in which the horns 3 are attached to both ends of the test specimen 6 is a mechanism which is used when applying average stress, in the invention, this mechanism is used so as to secure symmetry of the temperature distribution. That is, although the rod 4 and the horn 3 are not normally required under a test condition in which average stress is zero, in the device of the invention, the rod 4 and the horn 3 are mounted so as to secure symmetry of the temperature distribution even under this test condition.

Figure 2A:
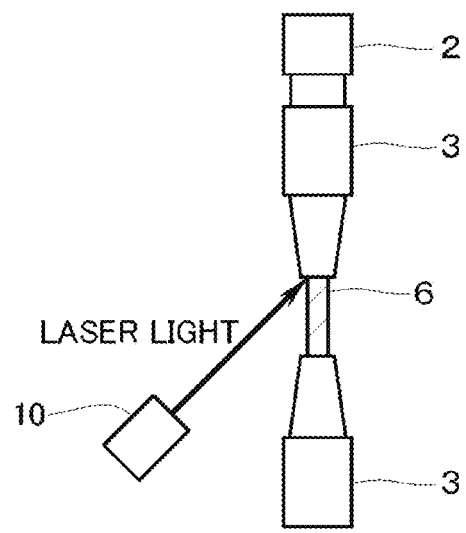
FIG. 2 is a conceptual diagram of an end surface displacement measurement in the method of the invention.

FIG. 2 is a conceptual diagram of an end surface displacement measurement by the method of the invention. As shown in FIG. 2(a), in the ultrasonic fatigue testing method, laser light is irradiated from an oblique direction using a laser displacement meter 10, and reflected laser light is received to measure end surface displacement of the test specimen 6.

Figure 2B:
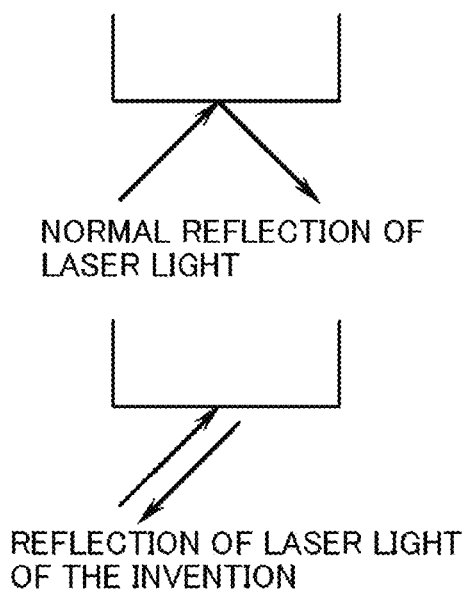

In the invention, as shown in FIG. 2(b), laser light is irradiated from an oblique direction using the laser displacement meter 10, and laser light reflected in the same direction is received to measure end surface displacement.

Figure 3A:
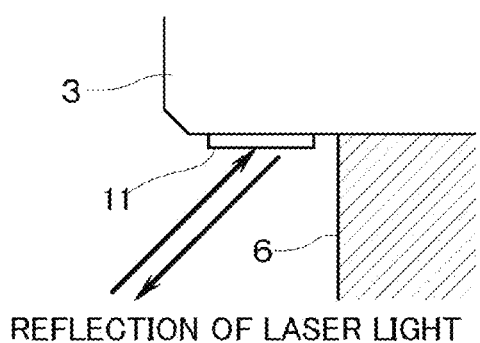
FIG. 3 is a diagram showing a method which reflects laser light irradiated from an oblique direction in the same direction.
Figure 3B:
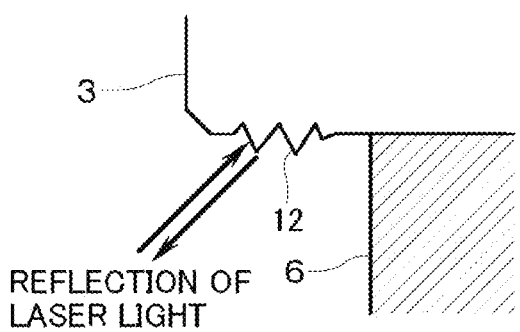
Figure 3C:
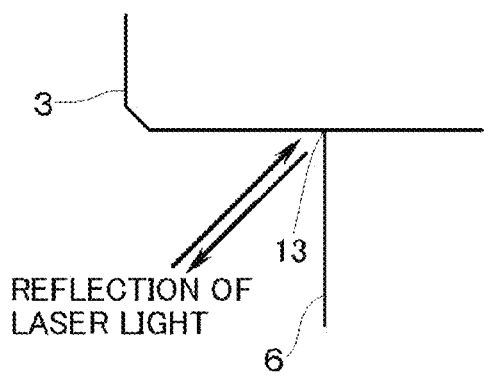
Figure 3D:
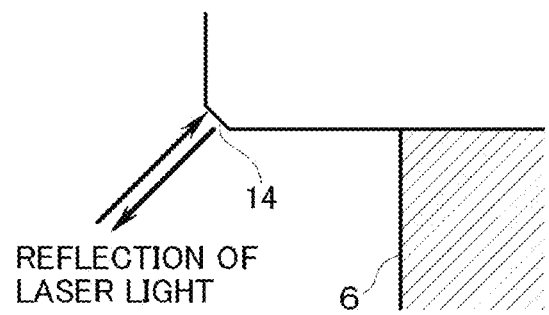

In this case, as a method of reflecting laser light in the same direction, there are a method in which, as shown in FIG. 3(a), a reflecting tape 11 is attached to the end surface of the rod 4, a method in which, as shown in FIG. 3(b), an artificial concavoconvex 12 is formed in the end surface of the rod 4, a method in which, as shown in FIG. 3(c), laser light is irradiated onto a corner 13 (a joint part of the test specimen and the rod), a method in which, as shown in FIG. 3(d), a chamfered part 14 is formed in the end surface of the rod 4 and used as a reflecting surface of laser light, and the like. Of these, as shown in FIG. 3(d), a method in which the chamfered part 14 is provided in the rod 4 is optimally used.

Figure 4:
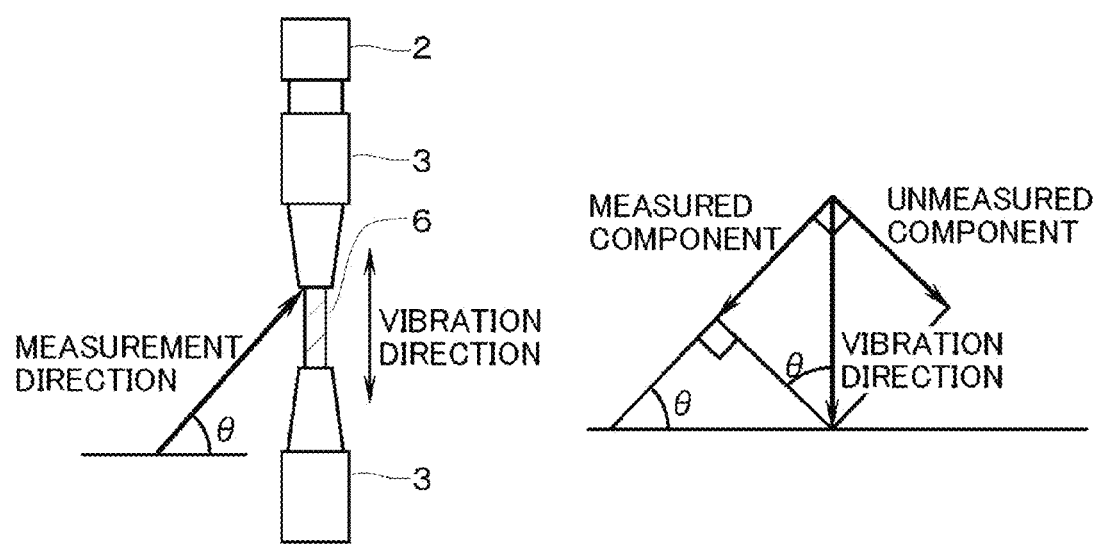
FIG. 4 is a diagram showing a component of displacement which is measured by the method of the invention.

In the method of the invention, as shown in FIG. 4, displacement of an irradiation direction component of laser light with respect to actual vibration is measured. In this case, actual displacement AO can be calculated from displacement AM to be measured using Expression (6).

[Math. 6]

$$AO = AM/\sin\theta \quad (6)$$

In the method of the invention, a black-body coating is coated on the test specimen using a two-color radiation thermometer to measure and control the temperature at the center of the test specimen.

First, a problem of visual field defect was solved using a two-color radiation thermometer. Although the two-color radiation thermometer uses a method in which two types of infrared rays having different wavelengths are received to perform a temperature measurement, since the temperature of a part at the highest temperature in the visual field can be measured, there is an extremely intensive effect on a problem of visual field defect.

However, even if the two-color radiation thermometer is used, it is not possible to solve a problem of emissivity change.

In principle, in the two-color radiation thermometer, although setting of emissivity is not required, instead, it is necessary to set the ratio of emissivity with respect to two infrared rays. Since the ratio of emissivity changes with surface oxidization, the two-color radiation thermometer substantially has a problem of emissivity change.

Since the lower limit of temperature which can be measured by the two-color radiation thermometer is about 400° C., the lower limit of temperature which can be controlled becomes about 500° C.

Accordingly, as a solution to the problem of emissivity change, a black-body coating having a high heat resistant temperature is coated on the surface of the test specimen.

The black-body coating is a coating which causes a coating film having known emissivity to be stuck to the measurement surface, thereby solving the problem of emissivity. However, in the case of a fatigue test, the coating film may interfere with oxidization of the surface of the test specimen, and may affect a fatigue test result. Accordingly, in the invention, the black-body coating is coated only on an extremely small part of the surface of the test specimen, and the temperature of the coated location is measured.

That is, it has been studied such that at least a part of the central part of the test specimen has no coating film, and a fatigue test can take the effect of oxidization into consideration.

In this case, since the upper limit of a heat resistant temperature of the black-body coating is 1500° C., the upper limit of a test temperature becomes 1500° C.

In the method of the invention, high-frequency heating is performed using a double-wound coil with a coil interval equal to or smaller than 20 mm.

That is, in the device configuration of the invention, although the temperature at the center of the test specimen 6 is measured and controlled by the radiation thermometer, when the number of turns of the coil is odd-numbered, the coil inhibits a temperature measurement.

Figure 8:
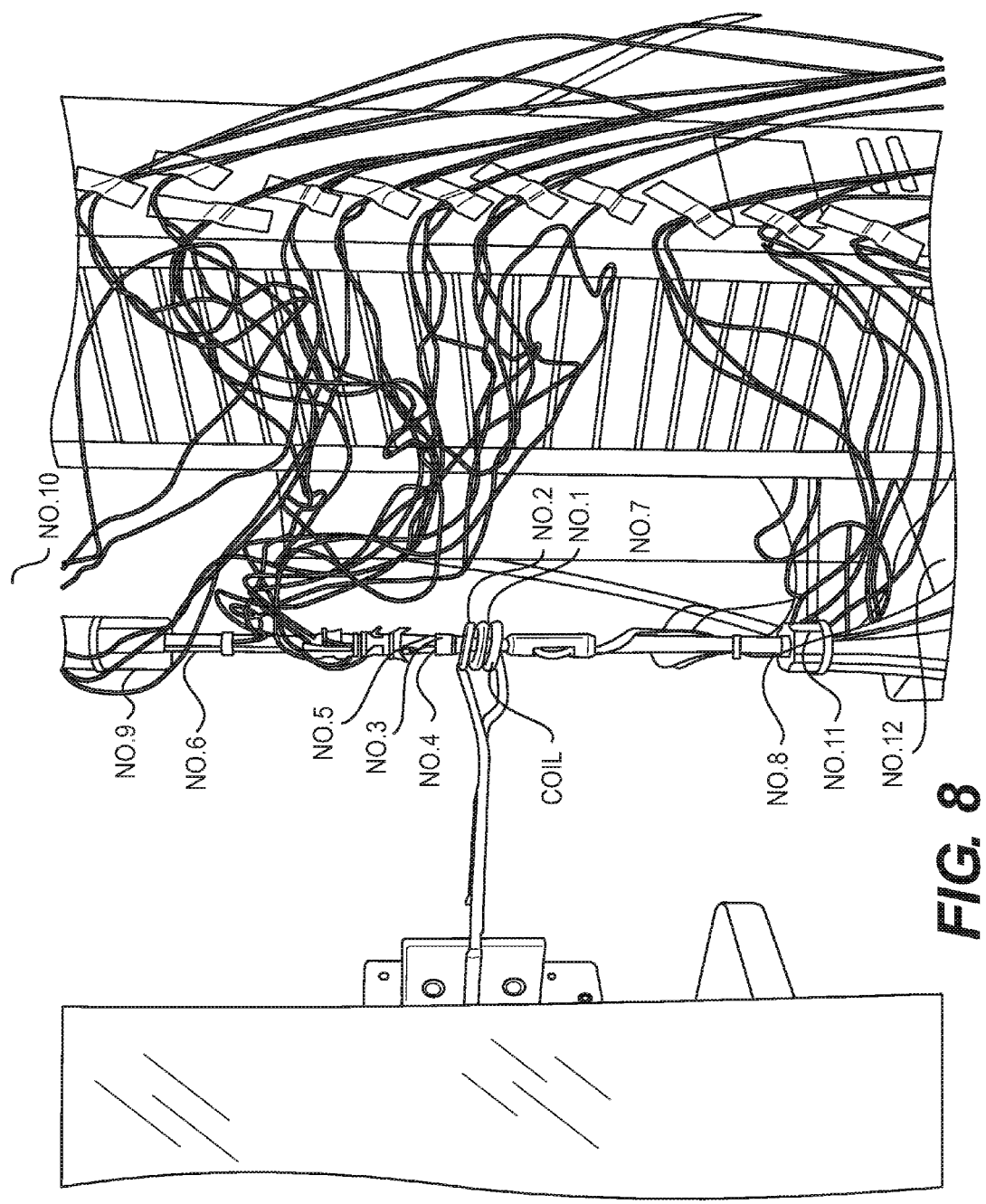
FIG. 8 is a photograph showing a specific device configuration of a testing device of the invention and a mode of a temperature distribution measurement. Nos. 1 to 12 denote the positions of thermocouples.

For example, in a triple-wound coil shown in FIG. 8, the second coil becomes an obstacle, making it difficult to perform a temperature measurement at the center of the test specimen 6.

Figure 5:
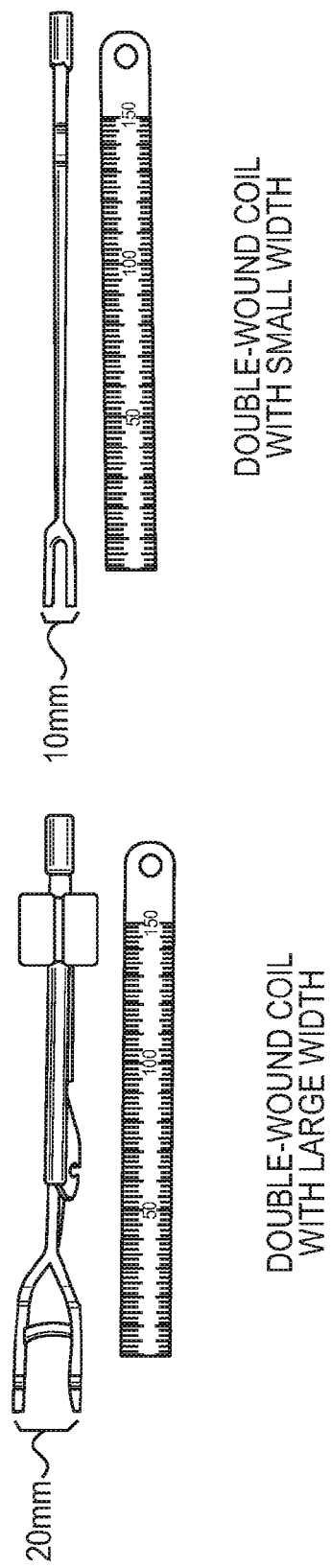
FIG. 5 is a photograph of two types of double-wound coils used so as to optimize a coil shape.

For this reason, although the number of turns of the coil should be even-numbered, since the test specimen 6 is small, the optimum number of turns is two as shown in FIG. 5.

In the case of the ultrasonic fatigue test, since the frequency is extremely high, the test specimen 6 itself generates heat depending on test conditions.

In order to perform temperature control so as to follow heat generation, the coil interval of the double-wound coil is preferably as small as possible. Specifically, it is preferable that high-frequency heating is performed using a coil having a coil interval equal to or smaller than 20 mm.

The invention is superior to the related art in that a problem regarding a test only of short lifespan since a high-temperature fatigue test of the related art is at low speed can be solved at once, and performance capable of realizing a fast fatigue test for testing up to long lifespan in a short time is obtained.

As a specific application example of the invention, there is fatigue property evaluation of a turbine blade material requiring fatigue properties up to long lifespan by fast vibration, or the like.

EXAMPLES

Hereinafter, although the invention will be described in more detail in connection to examples, the invention is not limited to these examples.

Example 1

Temperature dependency of Young's modulus was linearly approximated. Convergent calculation was performed using Young's modulus measured at room temperature and the L2 value measured at the test temperature, and temperature dependency of Young's modulus was obtained. Numerical calculation was performed using the Runge-Kutta formula.

Figure 6:
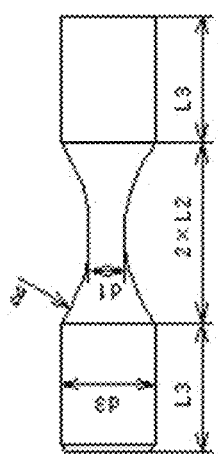
FIG. 6 shows a display screen of stress calculation software which is used in the method of the invention. A function of inversely calculating temperature dependency of Young's modulus is provided.

FIG. 6 shows a display screen of produced stress calculation software. This inverse calculation function of Young's modulus is incorporated.

Figure 7A:
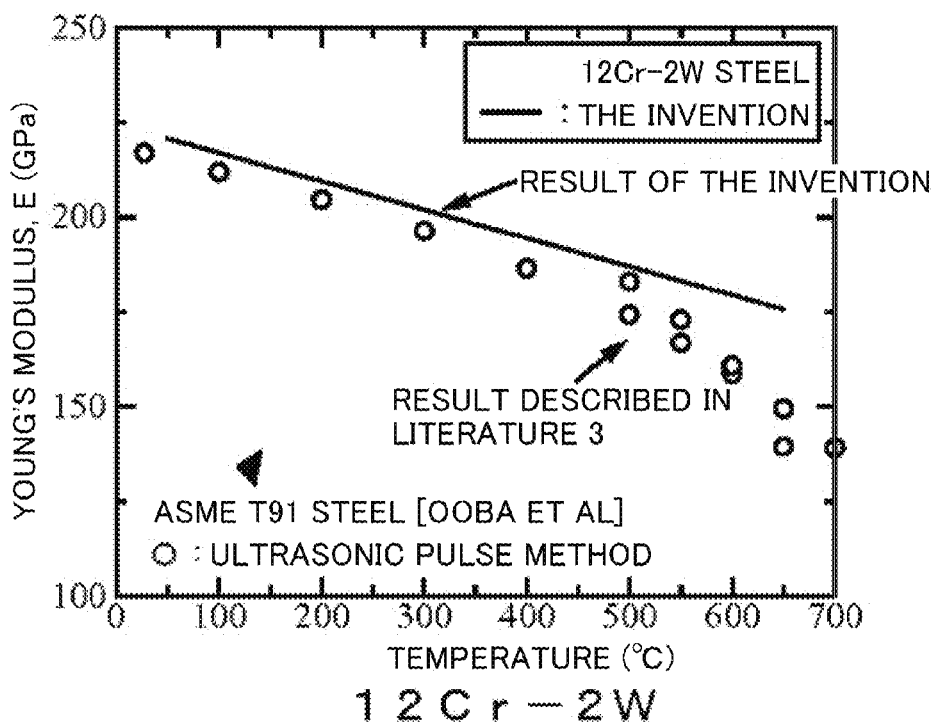
FIG. 7 is a graph showing comparison between Young's modulus obtained by the invention and the values of NPL2 and NPL3 of similar materials.
Figure 7B:
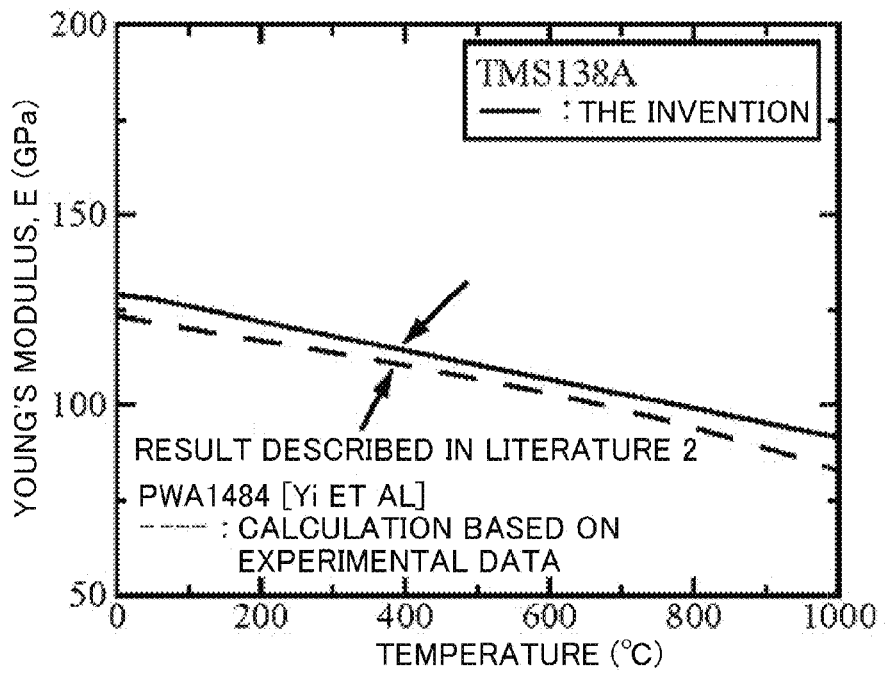

FIG. 7 shows the result of comparison between obtained Young's modulus and a literature value of Young's modulus of a material similar in component, microstructure, and strength.

Although (a) shows the results obtained for 12Cr-2W steel, this tends to match the literature value reported for ASME T91 steel well.

Although the result of this example tends to be higher at near 600° C., this is considered because, while 2% of tungsten (W) is added to the material measured in this example, no tungsten is added to the material of the literature. It is well known that, with the addition of tungsten, Young's modulus increases.

(b) shows the result of comparison between the result of this example for TMS138A and the literature value for PWA1484.

In all cases, although Ni-base single crystal alloy is a material which is used in a turbine blade, both tend to be well-matched. In this way, it has been confirmed that reliable Young's modulus can be obtained by the invention.

Example 2

The device of the invention shown in FIG. 1 having the rods and the horns attached to both ends of the test specimen was used.

A mode of a temperature distribution measurement in the configuration in which the rods and the horns are attached to both ends of the test specimen is shown in FIG. 8, and a measurement result is shown in Table 1.

Although Nos. 5 and 7 of FIG. 8 correspond to the temperature at the leading end of the rod, since both are substantially matched in temperature, it can be confirmed that the temperature distribution is symmetrical in the vertical direction.

Although the temperature at a position closest to the vibrator corresponds to No. 10, since the temperature of No. 10 is substantially about 30° C. even if heating at about 1000° C. is performed, it can be confirmed that sufficient heat insulation is obtained in the device configuration of this example.

The temperature distribution reaches a stationary state by heating for about two hours, and thereafter, even if heating is performed for up to 24 hours, the temperature distribution is not changed.

In this way, it was confirmed that it was possible to secure symmetry of the temperature distribution in the device configuration of this example and to obtain sufficient heat resistance.

TABLE 1

| Heating Time | Output (A) | Measurement Temperature (° C.) by Thermocouple | | | | | | | | | | | |
|---|---|---|---|---|---|---|---|---|---|---|---|---|---|
| | | No. 1 | No. 2 | No. 3 | No. 4 | No. 5 | No. 6 | No. 7 | No. 8 | No. 9 | No. 10 | No. 11 | No. 12 |
| 0 h | 0 | 24 | 24 | 24 | 24 | 24 | 24 | 24 | 24 | 24 | 24 | 24 | 24 |
| 0.5 h | 174 | 998 | 822 | 716 | 589 | 585 | 46 | 581 | 47 | 36 | 24 | 38 | 24 |
| 1 h | 174 | 996 | 821 | 715 | 586 | 583 | 49 | 578 | 49 | 40 | 27 | 41 | 28 |
| 2 h | 174 | 997 | 820 | 716 | 587 | 582 | 50 | 578 | 49 | 41 | 31 | 40 | 31 |
| 24 h | 174 | 997 | 822 | 714 | 588 | 584 | 50 | 580 | 50 | 40 | 31 | 41 | 31 |

Example 3

Figure 9:
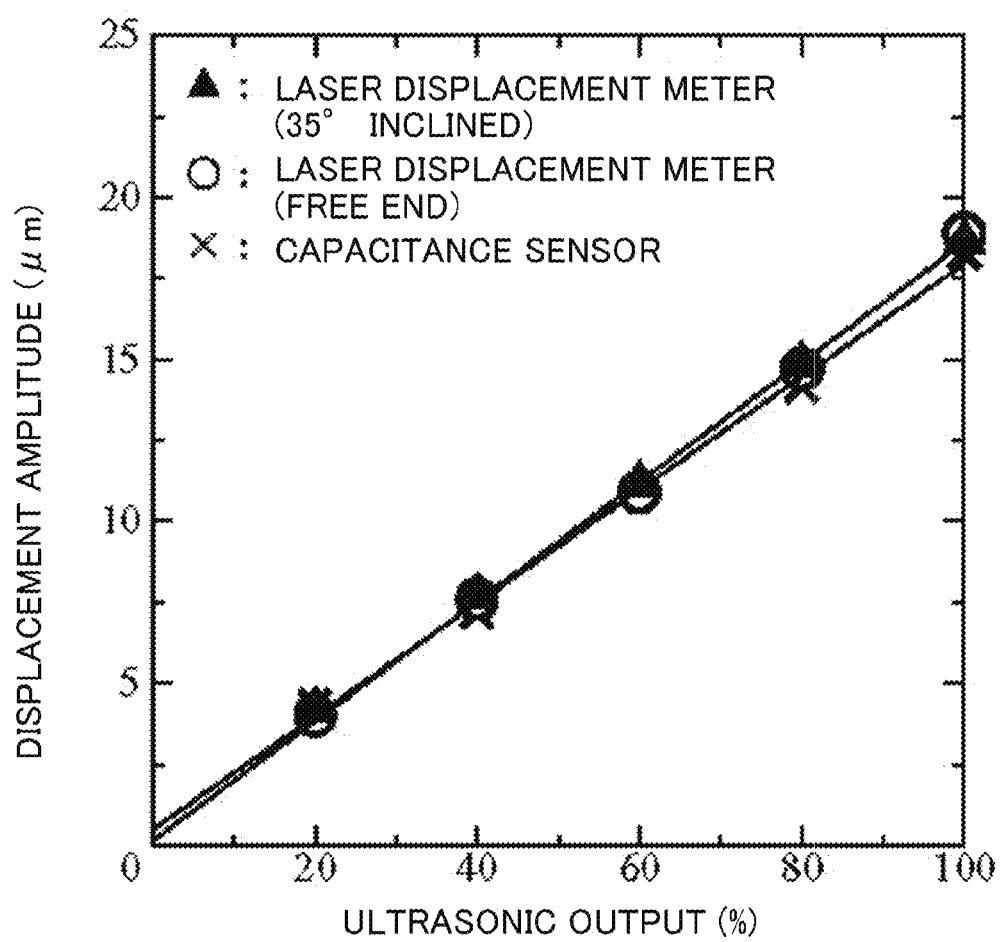
FIG. 9 is a graph showing the result of comparison between end surface displacement measured by the invention and end surface displacement measured by a normal method.

FIG. 9 shows the result of comparison between end surface displacement measured by the configuration of FIGS. 1 to 3 and end surface displacement measured using a normal free end.

Here, laser light was irradiated from a direction of 35° with respect to the horizontal direction, and a chamfered part (FIG. 3(*d*)) of 35° was provided in the horn (in this case, the rod) so as to be perpendicular with respect to the horn.

As will be apparent from FIG. 9, the measurement result of the invention matches the measurement result by the normal method well. That is, validity of the end surface displacement measurement of the invention was confirmed.

Example 4

The temperature of the central part of the test specimen is measured by both the thermocouple and the radiation thermometer, and the comparison result between the measured temperatures of both is shown in FIG. 10.

Figure 10A:
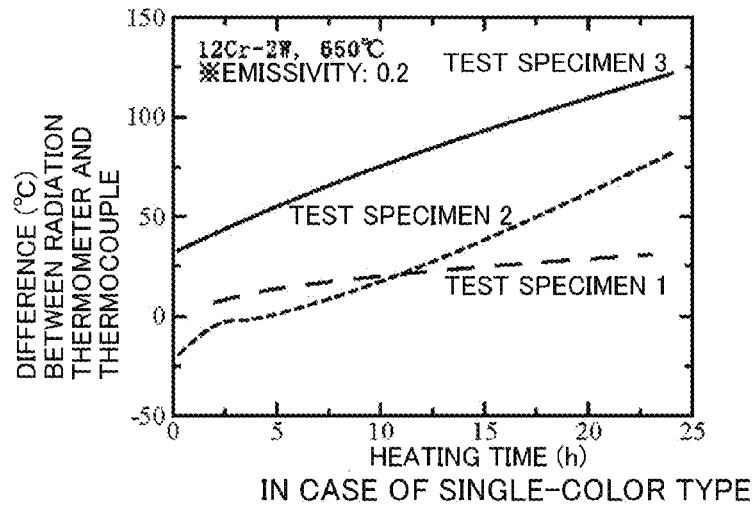
FIG. 10 is a graph showing the result of comparison between a measured temperature by a thermocouple under various conditions and a measured temperature by a radiation thermometer.

When a single-color radiation thermometer is used, as shown in FIG. 10(a), variation in the measured temperature between the test specimens increases. This is because, when the test specimen is attached to the device, the degree of visual field defect differs slightly between test specimens.

Although the measured temperature increases as the heating time elapses, this is caused by emissivity change due to oxidization of the surface of the test specimen.

Figure 10B:
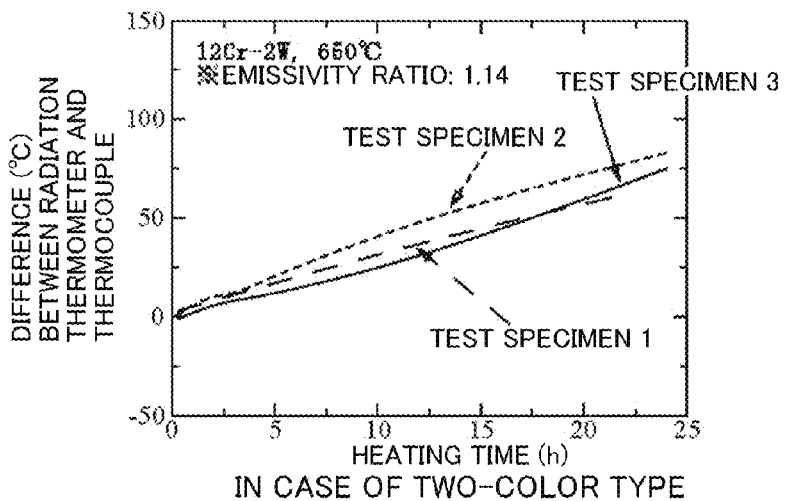

When the two-color radiation thermometer is used, as shown in FIG. 10(b), variation between the test specimens decreases. Accordingly, it can be understood that the problem of visual field defect is resolved.

However, since the measured temperature increases as the heating time elapses, the problem of emissivity change is not resolved.

Figure 10C:
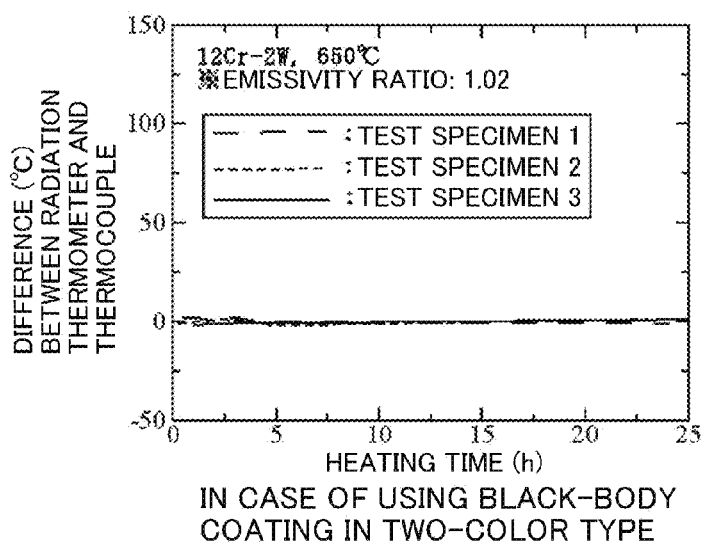

In contrast, when a black-body coating is coated on the test specimen and a measurement is made using the two-color radiation thermometer, as shown in FIG. 10(c), variation between the test specimens and an increase in temperature over time are not observed. Accordingly, it can be understood that the problem of emissivity change can be solved by coating the black-body coating.

In this case, validity of the temperature measurement method by the radiation thermometer in the configuration of this example was confirmed.

Example 5

In an ultrasonic fatigue test at 650° C. using 2Cr-2W steel, in regard to followability of temperature control with respect to heat generation of the test specimen, the result of examination on the difference between properties of two types of coils is shown in Table 2.

In an ultrasonic fatigue test, as a measure for suppressing heat generation of the test specimen, there is a method, such as an intermittent test, in which oscillation and stopping are repeated at a regular interval to reduce the effective frequency. Here, the allowable fluctuation range of the surface temperature of the test specimen is within ±5° C., and how much the effective frequency can be increased with respect to certain stress amplitude was compared between two types of coils.

lowability with respect to heat generation of the test specimen and to increase the effective rate when performing the ultrasonic fatigue test.

From this result, validity of the use of a double-wound coil having a small coil interval was confirmed.

Example 6

In order to examine the correlation between the fatigue test result by the method of the invention having the configuration of Examples 1 to 5 and the fatigue test result by the normal method, the fatigue test was performed for two types of materials of 12Cr-2W steel and Ni-base single crystal alloy, and comparison with the normal fatigue test results disclosed in NPLs 4 and 5 was made.

At this time, a test at 650° C. was performed for 12Cr-2W steel, and a test at 1000° C. was performed for Ni-base single crystal alloy.

The condition of the stress ratio R is R=−1 for complete alternation of tension and compression in the case of 12Cr-2W steel and R=0 for complete pulsation of only tension in the case of Ni-base single crystal alloy.

Figure 11A:
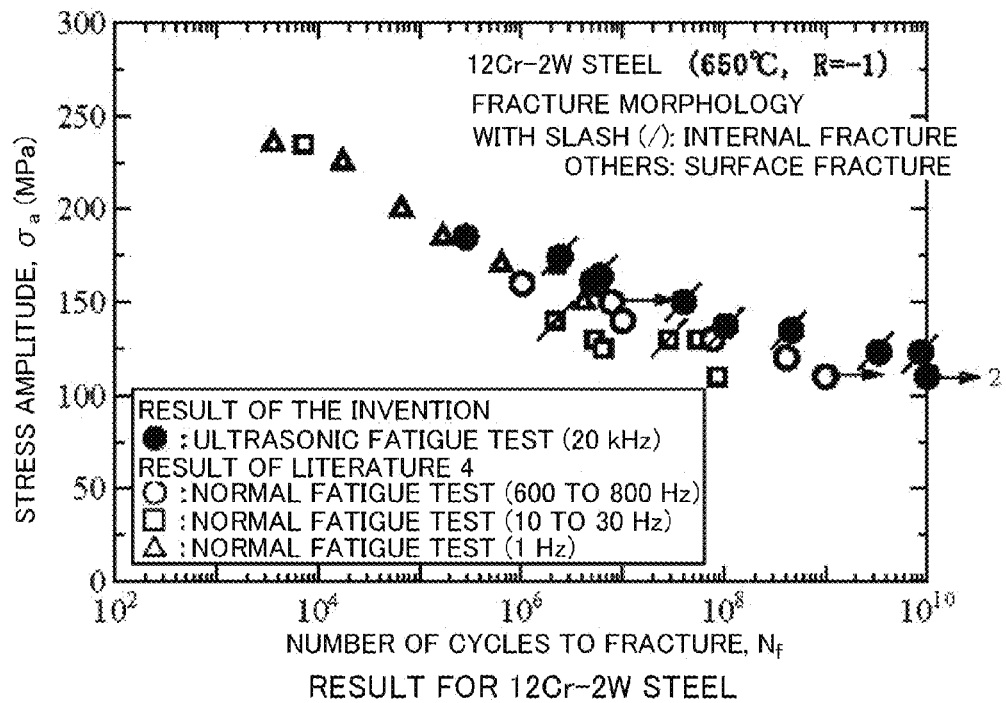
FIG. 11 is a graph showing the result of a fatigue test which is performed so as to verify validity of the device of the invention.
Figure 11B:
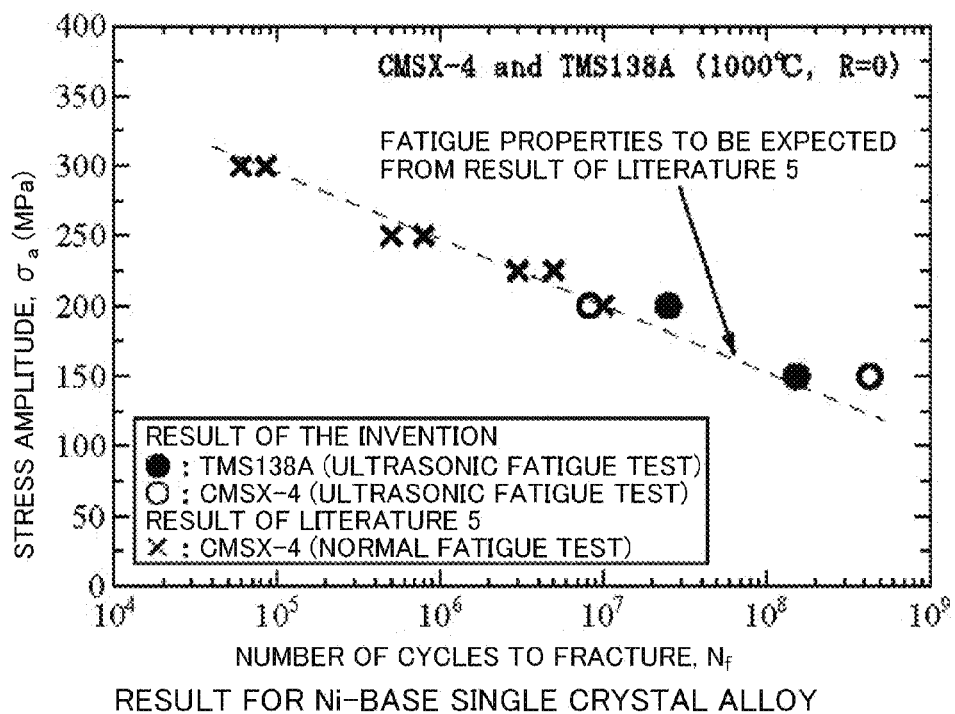
Figure 12:
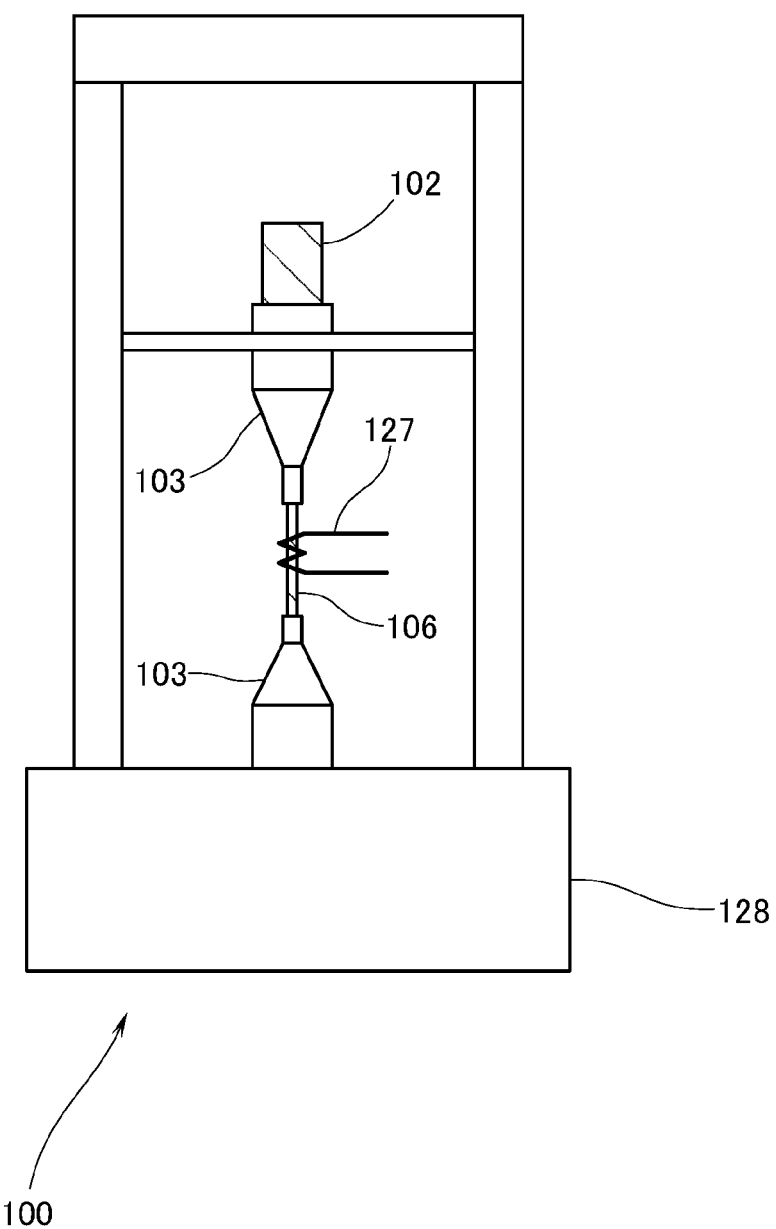
FIG. 12 is a schematic view of a basic configuration of a high-temperature ultrasonic fatigue testing device.

FIG. 11 shows the fatigue test result. In the case of 12Cr-2W steel, while the result of the invention tends to be on a somewhat high strength side, the difference from comparison data is very small.

In regard to Ni-base single crystal alloy, the result matches the normal fatigue test result well.

Here, in the results described in NPL 2, the result of the ultrasonic fatigue test shows fatigue strength significantly higher than the normal fatigue test result.

Accordingly, the result of FIG. 11 means that completeness of the method and device of the invention is very high.

In this way, it was confirmed that a correct fatigue test result was obtained by the invention.

REFERENCE SIGNS LIST

1: ultrasonic fatigue testing device
2: ultrasonic oscillation device
3: horn
4: rod

TABLE 2

| Material Type | Temperature (° C.) | Stress *1 (MPa) | Intermittent Test Condition *2 | | | Determination of Heat Generation *3 | |
|---|---|---|---|---|---|---|---|
| | | | On | Off | Effective Frequency | Large-Width Coil | Small-Width Coil |
| 12Cr—2W Steel | 650 | 140 | 110 | 5000 | 0.43 kHz | o | o |
| | | | 200 | 2000 | 1.82 kHz | o | o |
| | | | 200 | 500 | 5.7 kHz | x | o |
| | | 160 | 110 | 5000 | 0.43 kHz | o | o |
| | | | 200 | 2000 | 1.82 kHz | x | o |
| | | | 200 | 500 | 5.7 kHz | x | o |

*1: Stress amplitude to be applied by the ultrasonic fatigue test (20 kHz). The condition of a stress ratio is R = −1.
*2: A test method in which oscillation and stopping are repeated at a regular interval. On is an oscillation time, and Off is a stop time.
*3: An acceptance determination result when the allowable fluctuation range of the surface temperature is within ±5° C.

In Table 2, while the fluctuation range of the temperature in a coil having small width is within the allowable range under any conditions, in a coil having large width, if an effective rate increases, the fluctuation range exceeds the allowable range.

That is, it can be understood that, if the coil interval is made small, it is possible to improve temperature fol- 5: cradle
6: test specimen
10: laser displacement meter
11: reflecting tape
12: artificial concavoconvex
13: corner (joint part of test specimen and horn)
14: chamfered part 100: ultrasonic fatigue testing device
102: ultrasonic oscillation device
103: horn
106: test specimen
127: high-frequency heating coil
128: load frame (average load applying mechanism)
129: displacement sensor
130: ring-shaped capacitance sensor

The invention claimed is:

1. A method for ultrasonic fatigue testing at high temperature, wherein Young's modulus corresponding to temperature is calculated from a measurement result of a resonance frequency by inverse calculation, and a fatigue load condition is controlled, the method comprising:
   (a) calculating a shoulder part length (L2) by expressions (1) to (5), as follows:

$$U''(x) + P(x)U'(x) + k^2 U(x) = 0; \qquad (1)$$

$$P(x) = \frac{S'(x)}{S(x)}; \qquad (2)$$

$$k = 2\pi f \sqrt{\frac{\rho}{E}}; \qquad (3)$$

$$S(x) = \frac{\pi}{4}d1^2 \cosh^2(\alpha x)\alpha = \frac{1}{L1}\cosh^{-1}\left(\frac{d2}{d1}\right), \; 0 \le x \le L1; \text{ and} \qquad (4)$$

$$S(x) = \frac{\pi}{4}d2^2 \; L1 \le x \le L1 + L2; \qquad (5)$$

(b) measuring the shoulder part length (L2) using an ultrasonic fatigue testing device; and
   (c) searching Young's modulus when the shoulder part length (L2) calculated in step (a) and the shoulder part length (L2) measured in step (b) are identical.

2. The method for ultrasonic fatigue testing at high temperature according to claim 1,
   wherein rods and horns are attached to both ends of a test specimen to secure temperature symmetry of the test specimen.

3. The method for ultrasonic fatigue testing at high temperature according to claim 2,
   wherein laser light is irradiated in an oblique direction using a laser displacement meter, and laser light reflected in the same direction is received to measure end surface displacement of the test specimen.

4. The method for ultrasonic fatigue testing at high temperature according to claim 3,
   wherein a black-body coating is coated on the test specimen using a two-color radiation thermometer to measure and control a temperature at a center of the test specimen.

5. The method for ultrasonic fatigue testing at high temperature according to claim 4,
   wherein high-frequency heating is performed using a double-wound coil with a coil interval equal to or smaller than 20 mm.

6. The method for ultrasonic fatigue testing at high temperature according to claim 3,
   wherein high-frequency heating is performed using a double-wound coil with a coil interval equal to or smaller than 20 mm.

7. The ultrasonic fatigue testing device which performs the method for ultrasonic fatigue testing at high temperature according to claim 3, the ultrasonic fatigue testing device comprising:
   the rods; and
   the horns which are provided at ends of the rods opposite to the test specimen.

8. The method for ultrasonic fatigue testing at high temperature according to claim 2,
   wherein a black-body coating is coated on the test specimen using a two-color radiation thermometer to measure and control a temperature at a center of the test specimen.

9. The method for ultrasonic fatigue testing at high temperature according to claim 8,
   wherein high-frequency heating is performed using a double-wound coil with a coil interval equal to or smaller than 20 mm.

10. The method for ultrasonic fatigue testing at high temperature according to claim 2,
    wherein high-frequency heating is performed using a double-wound coil with a coil interval equal to or smaller than 20 mm.

11. The ultrasonic fatigue testing device which performs the method for ultrasonic fatigue testing at high temperature according to claim 2, the ultrasonic fatigue testing device comprising:
    the rods; and
    the horns which are provided at ends of the rods opposite to the test specimen.

12. The method for ultrasonic fatigue testing at high temperature according to claim 1,
    wherein laser light is irradiated in an oblique direction using a laser displacement meter, and laser light reflected in the same direction is received to measure end surface displacement of a test specimen.

13. The method for ultrasonic fatigue testing at high temperature according to claim 12,
    wherein a black-body coating is coated on the test specimen using a two-color radiation thermometer to measure and control a temperature at a center of the test specimen.

14. The method for ultrasonic fatigue testing at high temperature according to claim 13,
    wherein high-frequency heating is performed using a double-wound coil with a coil interval equal to or smaller than 20 mm.

15. The method for ultrasonic fatigue testing at high temperature according to claim 12,
    wherein high-frequency heating is performed using a double-wound coil with a coil interval equal to or smaller than 20 mm.

16. The ultrasonic fatigue testing device which performs the method for ultrasonic fatigue testing at high temperature according to claim 12, the ultrasonic fatigue testing device comprising:
    rods which are attached to both ends of the test specimen; and
    horns which are provided at ends of the rods opposite to the test specimen.

17. The method for ultrasonic fatigue testing at high temperature according to claim 1,
    wherein a black-body coating is coated on a test specimen using a two-color radiation thermometer to measure and control a temperature at a center of the test specimen.

18. The method for ultrasonic fatigue testing at high temperature according to claim 17,
    wherein high-frequency heating is performed using a double-wound coil with a coil interval equal to or smaller than 20 mm.

19. The method for ultrasonic fatigue testing at high temperature according to claim 1,
  wherein high-frequency heating is performed using a double-wound coil with a coil interval equal to or smaller than 20 mm.

20. The ultrasonic fatigue testing device which performs the method for ultrasonic fatigue testing at high temperature according to claim 1, the ultrasonic fatigue testing device comprising:
  rods which are attached to both ends of a test specimen; and
  horns which are provided at ends of the rods opposite to the test specimen.

* * * * *